United States Patent
Romuald (10) Patent No.: US 9,839,505 B2
(45) Date of Patent: Dec. 12, 2017

(54) PROSTHESIS COMPRISING A MESH AND A STRENGTHENING MEANS

(71) Applicant: Sofradim Production, Trévoux (FR)

(72) Inventor: Gaëtan Romuald, Bron (FR)

(73) Assignee: Sofradim Production, Trevoux (FR)

( * ) Notice: Subject to any disclaimer, the term of this patent is extended or adjusted under 35 U.S.C. 154(b) by 367 days.

(21) Appl. No.: 14/421,236

(22) PCT Filed: Sep. 24, 2013

(86) PCT No.: PCT/EP2013/069860
§ 371 (c)(1),
(2) Date: Feb. 12, 2015

(87) PCT Pub. No.: WO2014/048922
PCT Pub. Date: Apr. 3, 2014

(65) Prior Publication Data
US 2015/0238299 A1    Aug. 27, 2015

(30) Foreign Application Priority Data

Sep. 25, 2012   (FR) ..................... 12 58983

(51) Int. Cl.
*A61F 2/02* (2006.01)
*A61F 2/00* (2006.01)

(52) U.S. Cl.
CPC .... *A61F 2/0063* (2013.01); *A61F 2210/0004* (2013.01); *A61F 2210/0076* (2013.01);
(Continued)

(58) Field of Classification Search
CPC ............ A61F 2/0063; A61F 2002/0068; A61F 2220/0008; A61F 2220/0016; A61F 2220/0083
See application file for complete search history.

(56) References Cited

U.S. PATENT DOCUMENTS

| | | |
|---|---|---|
| 1,187,158 A | 6/1916 | Mcginley |
| 3,054,406 A | 9/1962 | Usher |
| 3,118,294 A | 1/1964 | Van Laethem |
| 3,124,136 A | 3/1964 | Usher |
| 3,272,204 A | 9/1966 | Charles et al. |

(Continued)

FOREIGN PATENT DOCUMENTS

| | | |
|---|---|---|
| CA | 1317836 C | 5/1993 |
| CN | 201879864 U | 6/2011 |

(Continued)

OTHER PUBLICATIONS

Malette, W. G. et al., "Chitosan, A New Hemostatic," Ann Th. Surg., Jul. 1983, pp. 55-58, 36.
(Continued)

*Primary Examiner* — Jonathan Miles
*Assistant Examiner* — Wade Miles (57) ABSTRACT

Prosthesis (1) comprising one porous mesh (2) comprising a first face and a second face opposite the first face, the prosthesis (1) comprising: —one porous strengthening means (6) which strengthens the mesh (2) and is intended to cover at least part of one of said first and second faces of the mesh (2), —fastening means for fastening the strengthening means (3) to the mesh (2), in a position fastened to the mesh (2), the strengthening means (6) covers a peripheral part (7) of one of said first and second faces of the mesh.

11 Claims, 1 Drawing Sheet

(52) U.S. Cl.
CPC .......... *A61F 2220/0016* (2013.01); *A61F 2220/0083* (2013.01); *A61F 2230/0019* (2013.01); *A61F 2230/0021* (2013.01); *A61F 2250/005* (2013.01); *A61F 2250/0023* (2013.01); *A61F 2250/0031* (2013.01)

(56) References Cited

U.S. PATENT DOCUMENTS

| | | |
|---|---|---|
| 3,276,448 A | 10/1966 | Usher |
| 3,320,649 A | 5/1967 | Naimer |
| 3,364,200 A | 1/1968 | Ashton et al. |
| 3,570,482 A | 3/1971 | Emoto et al. |
| 3,718,725 A | 2/1973 | Hamano |
| 4,006,747 A | 2/1977 | Kronenthal et al. |
| 4,060,081 A | 11/1977 | Yannas et al. |
| 4,173,131 A | 11/1979 | Pendergrass et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 4,976,737 A | 12/1990 | Leake |
| 5,002,551 A | 3/1991 | Linsky et al. |
| 5,015,584 A | 5/1991 | Brysk |
| 5,116,357 A | 5/1992 | Eberbach |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,195,542 A | 3/1993 | Gazielly et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,258,000 A | 11/1993 | Gianturco |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | McMurray |
| 5,350,583 A | 9/1994 | Yoshizato et al. |
| 5,356,432 A | 10/1994 | Rutkow et al. |
| 5,368,549 A | 11/1994 | McVicker |
| 5,368,602 A | 11/1994 | de la Torre |
| 5,370,650 A | 12/1994 | Tovey et al. |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,676,967 A | 10/1997 | Williams et al. |
| 5,681,568 A | 10/1997 | Goldin et al. |
| 5,686,090 A | 11/1997 | Schilder et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,702,416 A | 12/1997 | Kieturakis et al. |
| 5,709,934 A | 1/1998 | Bell et al. |
| 5,711,960 A | 1/1998 | Shikinami |
| 5,716,409 A | 2/1998 | Debbas |
| 5,720,981 A | 2/1998 | Eisinger |
| 5,732,572 A | 3/1998 | Litton |
| 5,743,917 A | 4/1998 | Saxon |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | McGregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |

(56) References Cited

U.S. PATENT DOCUMENTS

| | | |
|---|---|---|
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Kovac |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,090,116 A | 7/2000 | D'Aversa et al. |
| 6,113,623 A | 9/2000 | Sgro |
| 6,120,539 A | 9/2000 | Eldridge et al. |
| 6,132,765 A | 10/2000 | DiCosmo et al. |
| 6,143,037 A | 11/2000 | Goldstein et al. |
| 6,153,292 A | 11/2000 | Bell et al. |
| 6,162,962 A | 12/2000 | Hinsch et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,180,848 B1 | 1/2001 | Flament et al. |
| 6,197,325 B1 | 3/2001 | MacPhee et al. |
| 6,197,934 B1 | 3/2001 | DeVore et al. |
| 6,197,935 B1 | 3/2001 | Doillon et al. |
| 6,210,439 B1 | 4/2001 | Firmin et al. |
| 6,214,020 B1 | 4/2001 | Mulhauser et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,306,424 B1 | 10/2001 | Vyakarnam et al. |
| 6,312,474 B1 | 11/2001 | Francis et al. |
| 6,319,264 B1 | 11/2001 | Tormala et al. |
| 6,328,686 B1 | 12/2001 | Kovac |
| 6,334,872 B1 | 1/2002 | Termin et al. |
| 6,383,201 B1 | 5/2002 | Dong |
| 6,391,060 B1 | 5/2002 | Ory et al. |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,425,924 B1 | 7/2002 | Rousseau |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,485,503 B2 | 11/2002 | Jacobs et al. |
| 6,500,464 B2 | 12/2002 | Ceres et al. |
| 6,500,777 B1 | 12/2002 | Wiseman et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,610,006 B1 | 8/2003 | Amid et al. |
| 6,613,348 B1 | 9/2003 | Jain |
| 6,616,685 B2 | 9/2003 | Rousseau |
| 6,623,963 B1 | 9/2003 | Muller et al. |
| 6,630,414 B1 | 10/2003 | Matsumoto |
| 6,637,437 B1 | 10/2003 | Hungerford et al. |
| 6,638,284 B1 | 10/2003 | Rousseau et al. |
| 6,645,226 B1 | 11/2003 | Jacobs et al. |
| 6,652,594 B2 | 11/2003 | Francis et al. |
| 6,652,595 B1 | 11/2003 | Nicolo |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,670,018 B2 | 12/2003 | Fujita et al. |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,712,859 B2 | 3/2004 | Rousseau et al. |
| 6,719,795 B1 | 4/2004 | Cornwall et al. |
| 6,723,335 B1 | 4/2004 | Moehlenbruck et al. |
| 6,726,660 B2 | 4/2004 | Hessel et al. |
| 6,730,299 B1 | 5/2004 | Tayot et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,743,435 B2 | 6/2004 | DeVore et al. |
| 6,746,458 B1 | 6/2004 | Cloud |
| 6,752,834 B2 | 6/2004 | Geistlich et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul Malak et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,872,227 B2 | 3/2005 | Sump et al. |
| 6,893,653 B2 | 5/2005 | Abraham et al. |
| 6,896,904 B2 | 5/2005 | Spiro et al. |
| 6,926,723 B1 | 8/2005 | Mulhauser et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |

(56) References Cited

U.S. PATENT DOCUMENTS

| | | |
|---|---|---|
| 6,984,392 B2 | 1/2006 | Bechert et al. |
| 6,988,386 B1 | 1/2006 | Okawa et al. |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,025,063 B2 | 4/2006 | Snitkin et al. |
| 7,041,868 B2 | 5/2006 | Greene et al. |
| 7,060,103 B2 | 6/2006 | Carr, Jr. et al. |
| RE39,172 E | 7/2006 | Bayon et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,804 B2 | 1/2007 | Nicolo |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,556,598 B2 | 7/2009 | Rao |
| 7,594,921 B2 | 9/2009 | Browning |
| 7,614,258 B2 | 11/2009 | Cherok et al. |
| 7,615,065 B2 | 11/2009 | Priewe et al. |
| 7,662,169 B2 | 2/2010 | Wittmann |
| 7,670,380 B2 | 3/2010 | Cauthen, III |
| 7,682,381 B2 | 3/2010 | Rakos et al. |
| 7,709,017 B2 | 5/2010 | Tayot |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,789,888 B2 | 9/2010 | Bartee et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,900,484 B2 | 3/2011 | Cherok et al. |
| 7,931,695 B2 | 4/2011 | Ringeisen |
| 8,052,759 B2 | 11/2011 | Dupic et al. |
| 8,079,023 B2 | 12/2011 | Chen |
| 8,100,924 B2 | 1/2012 | Browning |
| 8,123,817 B2 | 2/2012 | Intoccia et al. |
| 8,142,515 B2 | 3/2012 | Therin et al. |
| 8,157,821 B2 | 4/2012 | Browning |
| 8,157,822 B2 | 4/2012 | Browning |
| 8,182,545 B2 | 5/2012 | Cherok et al. |
| 8,197,837 B2 | 6/2012 | Jamiolkowski et al. |
| 8,206,632 B2 | 6/2012 | Rousseau et al. |
| 8,215,310 B2 | 7/2012 | Browning |
| 8,317,872 B2 | 11/2012 | Adams |
| 8,323,675 B2 | 12/2012 | Greenawalt |
| 8,343,232 B2 | 1/2013 | Adzich et al. |
| 8,366,787 B2 | 2/2013 | Brown et al. |
| 8,435,307 B2 | 5/2013 | Paul |
| 8,470,355 B2 | 6/2013 | Skalla et al. |
| 8,562,633 B2 | 10/2013 | Cully et al. |
| 8,574,627 B2 | 11/2013 | Martakos et al. |
| 8,709,094 B2 | 4/2014 | Stad et al. |
| 8,734,471 B2 | 5/2014 | Deitch |
| 8,753,360 B2 | 6/2014 | Gleiman et al. |
| 8,758,800 B2 | 6/2014 | Stopek et al. |
| 8,784,294 B2 | 7/2014 | Goddard |
| 8,814,887 B2 | 8/2014 | Walther et al. |
| 8,828,092 B2 | 9/2014 | Toso et al. |
| 8,834,864 B2 | 9/2014 | Odar et al. |
| 8,846,060 B2 | 9/2014 | Archibald et al. |
| 8,865,215 B2 | 10/2014 | Ladet et al. |
| 8,877,233 B2 | 11/2014 | Obermiller et al. |
| 8,911,504 B2 | 12/2014 | Mathisen et al. |
| 8,920,370 B2 | 12/2014 | Sholev et al. |
| 8,956,373 B2 | 2/2015 | Ford et al. |
| 8,962,006 B2 | 2/2015 | Bayon et al. |
| 8,968,762 B2 | 3/2015 | Ladet et al. |
| 8,979,935 B2 | 3/2015 | Lozier et al. |
| 9,034,357 B2 | 5/2015 | Stopek |
| 9,113,993 B2 | 8/2015 | Lee |
| 9,211,175 B2 | 12/2015 | Stopek et al. |
| 9,216,075 B2 | 12/2015 | Bailly et al. |
| 2002/0087174 A1 | 7/2002 | Capello |
| 2002/0095218 A1 | 7/2002 | Carr et al. |
| 2003/0086975 A1 | 5/2003 | Ringeisen |
| 2003/0106346 A1 | 6/2003 | Matsumoto |
| 2003/0114937 A1 | 6/2003 | Leatherbury et al. |
| 2003/0133967 A1 | 7/2003 | Ruszczak et al. |
| 2003/0225355 A1 | 12/2003 | Butler |
| 2004/0034373 A1 | 2/2004 | Schuldt-Hempe et al. |
| 2004/0054376 A1 | 3/2004 | Ory et al. |
| 2004/0059356 A1 | 3/2004 | Gingras |
| 2004/0101546 A1 | 5/2004 | Gorman et al. |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0116696 A1 | 6/2006 | Odermatt et al. |
| 2006/0135921 A1 | 6/2006 | Wiercinski et al. |
| 2006/0147501 A1 | 7/2006 | Hillas et al. |
| 2006/0216320 A1 | 9/2006 | Kitazono et al. |
| 2006/0252981 A1 | 11/2006 | Matsuda et al. |
| 2006/0253203 A1 | 11/2006 | Alvarado |
| 2006/0282103 A1 | 12/2006 | Fricke et al. |
| 2007/0088391 A1 | 4/2007 | McAlexander et al. |
| 2007/0129736 A1 | 6/2007 | Solecki |
| 2007/0198040 A1 | 8/2007 | Buevich et al. |
| 2007/0299538 A1 | 12/2007 | Roeber |
| 2008/0091276 A1 | 4/2008 | Deusch et al. |
| 2008/0109017 A1 | 5/2008 | Herweck et al. |
| 2008/0113001 A1 | 5/2008 | Herweck et al. |
| 2008/0172071 A1 | 7/2008 | Barker |
| 2008/0255593 A1 | 10/2008 | St-Germain |
| 2009/0035341 A1 | 2/2009 | Wagener et al. |
| 2009/0036996 A1 | 2/2009 | Roeber |
| 2009/0068250 A1 | 3/2009 | Gravagna et al. |
| 2009/0105526 A1 | 4/2009 | Piroli Torelli et al. |
| 2009/0163936 A1 | 6/2009 | Yang et al. |
| 2009/0187197 A1 | 7/2009 | Roeber et al. |
| 2009/0192530 A1 | 7/2009 | Adzich et al. |
| 2009/0204129 A1 | 8/2009 | Fronio |
| 2009/0216338 A1 | 8/2009 | Gingras et al. |
| 2009/0270999 A1 | 10/2009 | Brown |
| 2009/0281558 A1 | 11/2009 | Li |
| 2009/0318752 A1 | 12/2009 | Evans et al. |
| 2010/0104608 A1 | 4/2010 | Abuzaina et al. |
| 2010/0318108 A1 | 12/2010 | Datta et al. |
| 2011/0015760 A1 | 1/2011 | Kullas |
| 2011/0144667 A1 | 6/2011 | Horton et al. |
| 2011/0190795 A1 | 8/2011 | Hotter et al. |
| 2011/0238094 A1 | 9/2011 | Thomas et al. |
| 2011/0251699 A1 | 10/2011 | Ladet |
| 2011/0257666 A1 | 10/2011 | Ladet et al. |
| 2012/0016388 A1 | 1/2012 | Houard et al. |
| 2012/0029537 A1 | 2/2012 | Mortarino |
| 2012/0065727 A1 | 3/2012 | Reneker et al. |
| 2012/0082712 A1 | 4/2012 | Stopek et al. |
| 2012/0116425 A1 | 5/2012 | Intoccia et al. |
| 2012/0150204 A1 | 6/2012 | Mortarino et al. |
| 2012/0165937 A1 | 6/2012 | Montanari et al. |
| 2012/0179175 A1 | 7/2012 | Hammell |
| 2012/0179176 A1 | 7/2012 | Wilson et al. |
| 2012/0197415 A1 | 8/2012 | Montanari et al. |

(56) References Cited

U.S. PATENT DOCUMENTS

| | | | | |
|---|---|---|---|---|
| 2013/0158571 | A1* | 6/2013 | Meneghin | A61F 2/0063 606/151 |
| 2014/0044861 | A1 | 2/2014 | Boey et al. | |
| 2014/0364684 | A1 | 12/2014 | Lecuivre | |

FOREIGN PATENT DOCUMENTS

| | | |
|---|---|---|
| DE | 19544162 C1 | 4/1997 |
| DE | 19718903 A1 | 12/1997 |
| DE | 19751733 A1 | 12/1998 |
| DE | 19832634 A1 | 1/2000 |
| DE | 10019604 A1 | 10/2001 |
| DE | 10120942 A1 | 10/2001 |
| DE | 10043396 C1 | 6/2002 |
| EP | 0194192 A1 | 9/1986 |
| EP | 0248544 A1 | 12/1987 |
| EP | 0263360 A2 | 4/1988 |
| EP | 0276890 A2 | 8/1988 |
| EP | 0372969 A1 | 6/1990 |
| EP | 0531742 A1 | 3/1993 |
| EP | 544485 A1 | 6/1993 |
| EP | 0552576 A1 | 7/1993 |
| EP | 0611561 A1 | 8/1994 |
| EP | 614650 A2 | 9/1994 |
| EP | 0621014 A1 | 10/1994 |
| EP | 0625891 A1 | 11/1994 |
| EP | 0637452 A1 | 2/1995 |
| EP | 0664132 A1 | 7/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0800791 A1 | 10/1997 |
| EP | 827724 A2 | 3/1998 |
| EP | 0836838 A1 | 4/1998 |
| EP | 0847727 A1 | 6/1998 |
| EP | 0876808 A1 | 11/1998 |
| EP | 0895762 A2 | 2/1999 |
| EP | 898944 A2 | 3/1999 |
| EP | 1017415 A1 | 7/2000 |
| EP | 1036545 A2 | 9/2000 |
| EP | 1052319 A1 | 11/2000 |
| EP | 1055757 A1 | 11/2000 |
| EP | 1090590 A2 | 4/2001 |
| EP | 1 216 717 A1 | 6/2002 |
| EP | 1 216 718 A1 | 6/2002 |
| EP | 0693523 B1 | 11/2002 |
| EP | 1273312 A2 | 1/2003 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1645232 A1 | 4/2006 |
| EP | 1674048 A1 | 6/2006 |
| EP | 1691606 A1 | 8/2006 |
| EP | 1782848 A2 | 5/2007 |
| EP | 2229918 A1 | 9/2010 |
| EP | 2 305 132 A1 | 4/2011 |
| EP | 2404571 A1 | 1/2012 |
| EP | 2866729 A1 | 5/2015 |
| FR | 2244853 A1 | 4/1975 |
| FR | 2257262 A1 | 8/1975 |
| FR | 2 308 349 A1 | 11/1976 |
| FR | 2453231 A1 | 10/1980 |
| FR | 2612392 A1 | 9/1988 |
| FR | 2715309 A1 | 7/1995 |
| FR | 2715405 A1 | 7/1995 |
| FR | 2 724 563 A1 | 3/1996 |
| FR | 2730406 A1 | 8/1996 |
| FR | 2744906 A1 | 8/1997 |
| FR | 2766698 A1 | 2/1999 |
| FR | 2771622 A1 | 6/1999 |
| FR | 2773057 A1 | 7/1999 |
| FR | 2774277 A1 | 8/1999 |
| FR | 2779937 A1 | 12/1999 |
| FR | 2859624 A1 | 3/2005 |
| FR | 2863277 A1 | 6/2005 |
| FR | 2876020 A1 | 4/2006 |
| FR | 2884706 A1 | 10/2006 |
| FR | 2929834 A1 | 10/2009 |
| FR | 2953709 A1 | 6/2011 |
| FR | 2962645 A1 | 1/2012 |
| GB | 1174814 A | 12/1969 |
| GB | 2 051 153 A | 1/1981 |
| GB | 2306110 A | 4/1997 |
| JP | H0332677 A | 2/1991 |
| JP | H05237128 A | 9/1993 |
| JP | H09137380 A | 5/1997 |
| JP | H11146888 A | 6/1999 |
| JP | 2008538300 A | 10/2008 |
| JP | 2011078767 A | 4/2011 |
| WO | 89/02445 A1 | 3/1989 |
| WO | 89/08467 A1 | 9/1989 |
| WO | 90/12551 A1 | 11/1990 |
| WO | 92/06639 A2 | 4/1992 |
| WO | 92/20349 A1 | 11/1992 |
| WO | 93/11805 A1 | 6/1993 |
| WO | 9310731 A1 | 6/1993 |
| WO | 93/18174 A1 | 9/1993 |
| WO | 94/17747 A1 | 8/1994 |
| WO | 95/07666 A1 | 3/1995 |
| WO | 95/18638 A1 | 7/1995 |
| WO | 95/32687 A1 | 12/1995 |
| WO | 96/03091 A1 | 2/1996 |
| WO | 96/08277 A1 | 3/1996 |
| WO | 96/09795 A1 | 4/1996 |
| WO | 96/14805 A1 | 5/1996 |
| WO | 96/41588 A1 | 12/1996 |
| WO | 97/35533 A1 | 10/1997 |
| WO | 98/35632 A1 | 8/1998 |
| WO | 98/49967 A1 | 11/1998 |
| WO | 99/05990 A1 | 2/1999 |
| WO | 99/06079 A1 | 2/1999 |
| WO | 99/06080 A1 | 2/1999 |
| WO | 99/51163 A1 | 10/1999 |
| WO | 00/16821 A1 | 3/2000 |
| WO | 00/67663 A1 | 11/2000 |
| WO | 01/15625 A1 | 3/2001 |
| WO | 01/80773 A1 | 11/2001 |
| WO | 01/81667 A1 | 11/2001 |
| WO | 02/07648 A1 | 1/2002 |
| WO | 0217853 A2 | 3/2002 |
| WO | WO 02/22047 A1 | 3/2002 |
| WO | 02/078568 A1 | 10/2002 |
| WO | 03/002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 2005011280 A1 | 2/2005 |
| WO | 2005013863 A2 | 2/2005 |
| WO | 2005018698 A1 | 3/2005 |
| WO | 2005048708 A1 | 6/2005 |
| WO | 2005105172 A1 | 11/2005 |
| WO | 2006018552 A1 | 2/2006 |
| WO | 2006023444 A1 | 3/2006 |
| WO | 2007048099 A2 | 4/2007 |
| WO | 2009031035 A2 | 3/2009 |
| WO | 2009071998 A2 | 6/2009 |
| WO | 2010043978 A2 | 4/2010 |
| WO | 2011007062 A1 | 1/2011 |
| WO | 2011026987 A1 | 3/2011 |
| WO | 2011038740 A1 | 4/2011 |
| WO | WO 2011/119845 A1 | 9/2011 |
| WO | 2012007579 A1 | 1/2012 |
| WO | 2014001508 A1 | 1/2014 |

OTHER PUBLICATIONS

Langenbech, M. R. et al., "Comparison of biomaterials in the early postoperative period," Surg Endosc., May 2003, pp. 1105-1109, 17 (7).

(56) References Cited

OTHER PUBLICATIONS

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.

Klinge, U. et al., "Foreign Body Reaction to Meshes Used for the Repair of Abdominal Wall Hernias," Eur J. Surg, Sep. 1999, pp. 665-673, 165.

Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).

Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.

Junge, K. et al., "Functional and Morphologic Properties of a Modified Mesh for Inguinal Hernia Repair," World J. Surg., Sep. 2002, pp. 1472-1480, 26.

Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.

Welty, G. et al., "Functional impairment and complaints following incisional hernia repair with different polypropylene meshes," Hernia, Aug. 2001; pp. 142-147, 5.

Varum, K. et al., "In vitro degradation rates of partially N-acetylated chitosans in human serum," Carbohydrate Research, Mar. 1997, pp. 99-101, 299.

Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).

Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220,18(2).

Blondin, C. et al., "Inhibition of Complement Activation by Natural Sulfated Polysaccharides (Fucans) from Brown Seaweed," Molecular Immuol., Mar. 1994, pp. 247-253, 31(4).

Zvyagintseva, T. et al., "Inhibition of complement activation by water-soluble polysaccharides of some far-eastern brown seaweeds," Comparative Biochem and Physiol, Jul. 2000, pp. 209-215,126(3).

Rosen, M. et al., "Laparoscopic component separation in the single-stage treatment of infected abdominal wall prosthetic removal," Hernia, 2007, pp. 435-440, 11, published online Jul. 2007.

Amid, P., "Lichtenstein tension-free hernioplasty: Its inception, evolution, and principles," Hernia, 2004; pp. 1-7, 8, published online Sep. 2003.

Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).

O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).

Muzzarelli, R. et al., "Reconstruction of parodontal tissue with chitosan," Biomaterials, Nov. 1989, pp. 598-604, 10.

Haroun-Bouhedja, F. et al., "Relationship between sulfate groups and biological activities of fucans," Thrombosis Res., Dec. 2000, pp. 453-459, 100(5).

Blondin, C. et al., "Relationships between chemical characteristics and anticomplementary activity of fucans," Biomaterials, Mar. 1996, pp. 597-603, 17(6).

Strand, S. et al., "Screening of Chitosans and Conditions for Bacterial Flocculation," Biomacromolecules, Mar. 2001, 126-133, 2.

Kanabar, V. et al., "Some structural determinants of the antiproliferative effect of heparin-like molecules on human airway smooth muscle," Br. J. Pharmacol., Oct. 2005, pp. 370-777, 146(3).

Hirano, S. et al., "The blood biocompatibility of chitosan and N-acylchitosans," J. Biomed. Mater. Res., Apr. 1985, 413-417, 19.

Rao, B. et al., "Use of chitosan as a biomaterial: Studies on its safety and hemostatic potential," J. Biomed. Mater. Res., Jan. 1997, pp. 21-28, 34.

Prokop, A. et al., "Water Soluble Polymers for Immunoisolation I: Complex Coacevation and Cytotoxicity," Advances in Polymer Science, Jul. 1998, pp. 1-51, 136.

Collins, R. et al., "Use of collagen film as a dural substitute: Preliminary animal studies," Journal of Biomedical Materials Research, Feb. 1991, pp. 267-276, vol. 25.

Dr. S. Raz, "The Karl Mayer Guide to Tehnical Textiles," Jan. 2000, pp. 1-36, Obertshausen, Germany.

Chen, G. et al., "A Hybrid Network of Synthetic Polymer Mesh and Collagen Sponge," The Royal Society of Chemistry 2000, Chem. Commun., Jul. 2000, pp. 1505-1506.

European Office Action issued in corresponding European Patent Application No. 13774096.5 dated Oct. 4, 2016, 5 pages.

European Office Action dated Apr. 11, 2016 in corresponding European Patent Application No. 13774096.5, 6 pages.

International Search Report for PCT/EP13/069860 date of completion is Jan. 15, 2014 (3 pages).

\* cited by examiner

PROSTHESIS COMPRISING A MESH AND A STRENGTHENING MEANS

CROSS-REFERENCE TO RELATED APPLICATIONS

This application is a National Stage Application of PCT/EP13/069860 under 35 USC §371 (a), which claims priority of French Patent Application Serial No. 12/58983 filed Sep. 25, 2012, the disclosures of each of the above-identified applications are hereby incorporated by reference in their entirety.

The present invention relates to a prosthesis for medical or surgical use.

In the treatment of parietal insufficiencies, such as hernias and incisional hernias, the role of the prosthesis is to provide mechanical support to the surgical reconstruction. The prosthesis is often in the form of a piece of biocompatible textile which may or may not be accompanied by additional elements such as a coating in the form of a film, a set of needles, etc. The prosthesis is all the more effective, and its local tolerance all the better, if it integrates in the tissue intimately and at an early stage. To achieve intimate and early integration without formation of a peripheral fibrous shell, the pores of the prosthesis must be as widely open as possible to the outside, and its elasticity must allow it to follow the physiological deformations of the wall.

In a known manner, such prostheses, also called prosthetic fabrics or knits, have to meet a number of requirements, and in particular they need to have a mechanical strength in at least two perpendicular directions, be biocompatible, flexible and conformable, while having a certain capacity for elongation, in at least one direction, be porous and able to be sutured and recut, while at the same time being non-tear and run-proof, and, finally, they must be sterilizable. In general, the prostheses are knitted and made up of several sheets of interlaced yarns in order to meet all of these requirements. Thus, a large amount of foreign material is present in the long term in the body of the patient when the prosthetic material is not absorbable. This is undesirable, since the foreign material is likely to cause inflammation or fibrous shells in the body of the patient.

There is therefore a need for a prosthesis which has sufficient mechanical strength at least during the period of cell recolonization and which avoids any risk of recurrence, while at the same time having minimal material, and which can be put in place simply and quickly.

There is also a need for a prosthesis that would favour cell colonization and that may be secured to the biological tissues with fixation means such as staples or stitches without risking to damage the mesh forming the prosthesis or to create local tears, and if possible while implanting as less as possible of foreign material in the body of the patient.

The present invention aims to solve at least one of these problems by making available a prosthesis for medical or surgical use, comprising at least one porous mesh made of biocompatible material, said mesh comprising a first face and a second face opposite the first face, the prosthesis additionally comprising:

- at least one strengthening means which strengthens the mesh and is intended to cover at least part of one of said first and second faces of the mesh,
- at least fastening means for fastening the strengthening means to the mesh, wherein the strengthening means is porous, the pores of the mesh having dimensions larger than those of the pores of the strengthening means, and in a position fastened to the mesh, the strengthening means covers a peripheral part of one of said first and second faces of the mesh.

In the present document, "mesh" is understood as an arrangement or assembly of biocompatible yarns, fibres, monofilaments and/or multifilaments, for example a knit, woven fabric, nonwoven fabric, preferably openworked, that is to say provided with pores that promote cell recolonization. The mesh is sufficiently flexible to be folded back on itself at the time of its introduction into the biological cavity. The mesh can be produced from one or more layers of yarn arrangements. Such meshes are well known to a person skilled in the art. The mesh that can be used according to the invention can be supplied in any shape, e.g. rectangular, square, circular, oval, etc., and can then be cut in order to be adapted to the shape of the hernia defect. For example, the mesh can have the general shape of a disc or an oval. Alternatively, the mesh can have a generally square or rectangular shape.

In the present invention, the adjective "porous" refers to a material having pores, voids or alveoli that promote cell colonization. The larger the pores of the mesh, the greater its ability to allow cell colonization.

In the present document, "strengthening means" is understood as a means of modifying, in particular increasing, the mechanical strength of the mesh in at least one direction, preferably in at least two perpendicular directions. For example, if the mesh is a knit, the strengthening means can increase the tear strength and/or the resistance to elongation in multiple directions.

In the present document, "fastening means" is understood as a means permitting reversible fixation of the strengthening means to the mesh, so as to permit detachment by pulling, for example, on the strengthening means. Of course, renewed fixation of the strengthening means, for example for repositioning, is possible at the time of manufacture of the prosthesis according to the invention.

Thus, the means of fastening the mesh according to the invention gives the prosthesis locally different mechanical properties, making it possible to treat parietal insufficiencies according to local specific stresses. Moreover, the possibility of covering only part of the mesh makes it possible to limit the quantity of foreign material of the prosthesis of the invention compared to a prosthesis of which the mesh is completely covered. Moreover, the fastening means according to the invention permit reversible fixation of the strengthening means, which can thus be repositioned on the mesh.

In addition, the prosthesis of the invention, allows an excellent cell recolonization with as less as possible of implanted foreign material in the biological tissues, together with a high resitance against potential tearing or rupture of the mesh.

It is conceivable that these prostheses according to the invention are supplied in modular form with, on the one hand, a mesh and, on the other hand, a strengthening means to be fastened to the mesh.

The strengthening means of the invention can be in any conceivable form, for example in any geometric shape, such as an oval, circle, rectangle, square, etc.

The mesh and the strengthening means according to the invention can also be made available in the form of a band, such that the elements of the prosthesis can be cut out in the required dimensions before fastening them.

Moreover, the prosthesis according to the invention can be supplied in an already defined form, with the strengthening means already positioned on and fastened to the mesh.

The strengthening means is porous, and the pores of the mesh have dimensions larger than those of the pores of the strengthening means. Thus, the presence of the strengthening means on a localized part of the mesh gives the prosthesis mechanical strength and reduces the capacity for elongation in a region of the prosthesis designed to effectively fill a tissue defect. In the other regions, which are not intended to fill a defect, a mesh with less mechanical strength may suffice. It is thus possible to use a mesh with large pores facilitating cell colonization and reducing the overall quantity of foreign material in the body of the patient.

Preferably, the strengthening means comprises at least one piece of textile made of biocompatible material. In the present document, "textile" is understood as an arrangement or assembly of biocompatible yarns, fibres, monofilaments and/or multifilaments, for example a knit, woven fabric and nonwoven fabric. In one embodiment, the textile is a knit. In another embodiment, the textile is a nonwoven fabric. The covering of a part of the mesh is thus facilitated by the flexibility of the textile, which can be easily dimensioned.

In one embodiment, the fastening means are situated on the strengthening means and/or on one or both of said first and second faces of the mesh. The strengthening means is then easily fastened to one of the faces of the mesh.

Preferably, the fastening means comprise barbs. In the present document, "barb" means any hook made of any biocompatible material and integral with the arrangement of yarns forming the mesh or with the arrangement of yarns forming the strengthening means when the latter is in the form of a piece of textile, whether these hooks have been incorporated in said arrangement during manufacture (braiding, knitting, weaving etc.) or have been added afterwards. Examples of knits comprising such barbs are described in the document WO01/81667.

The presence of the barbs is advantageous in that they allow the textile of the strengthening means to be locked onto the mesh. This locking, which is effective even in a liquid environment, is sufficient to ensure the fixation of the strengthening means to the mesh while at the same time permitting release of the strengthening means in order to adjust the position thereof with respect to the mesh if need be. This gives the prosthesis according to the invention great flexibility and a great capacity for adaptation.

In one embodiment, the strengthening means comprises a bioabsorbable material, and the mesh comprises a partially bioabsorbable material.

In the present document, "bioabsorbable" or "biodegradable" is understood as the characteristic by which a material is absorbed and degraded by the biological tissues and disappears in vivo after a given period which, for example, can vary from several hours to several months, depending on the chemical nature of the material.

Thus, the bioabsorbable materials suitable for the yarns of the mesh or of the textile of the strengthening means of the present invention can be chosen from among polylactic acid (PLA), polyglycolic acid (PGA), oxidized cellulose, chitosan, polyphosphazene, polycaprolactone (PCL), polydioxanone (PDO), trimethylene carbonate (TMC), polyvinyl alcohol (PVA), polyhydroxyalkanoates (PHAs), polyamides, polyethers, copolymers thereof, and mixtures thereof. In the present invention, "partially bioabsorbable" refers to a material formed by the combination of a bioabsorbable material and of a non-bioabsorbable material.

The non-bioabsorbable materials suitable for the mesh and the textile of the strengthening means of the present invention can be chosen from among polyethylene terephthalate (PET), polyamides, aramids, expanded polytetrafluoroethylene, polyurethane, polyvinylidene difluoride (PVDF), polybutyl esters, PEEK (polyether ether ketone), polyolefins (such as polyethylene or polypropylene), copper alloys, silver alloys, platinum, medical grades of steel such as medical-grade stainless steel, and combinations thereof.

In another embodiment, the mesh is composed of a single material, in particular a partially bioabsorbable material.

Alternatively or in addition, the strengthening means is composed of a single material, in particular a bioabsorbable material.

In the configuration in which the mesh is composed of only a single partially bioabsorbable material and in which the strengthening means is composed of only a single bioabsorbable material, the prosthesis introduced into the human body initially comprises both the material of the mesh and also that of the strengthening means. During the weeks following the implantation, in particular permitting cell colonization, the bioabsorbable material disappears and the partially bioabsorbable material disappears in part. Thus, when the tissue defect has been filled by the cell recolonization, the materials constituting the prosthesis disappear at least partially. The overall quantity of residual foreign material in the body is thus greatly reduced. More precisely, the material of the strengthening means of the mesh is intended to completely disappear once the strengthening of the mesh has been rendered superfluous by the repair of the biological tissue. The material of the mesh is intended to partially disappear, so as to provide a minimal reinforcement over the entirety of the surface of the biological tissue treated by the prosthesis. This makes it possible to avoid any risk of recurrence, while at the same time permitting a reduction in the quantity of residual foreign material.

According to one alternative, the strengthening means comprises a partially bioabsorbable material, and the mesh comprises a bioabsorbable material.

According to one embodiment, the strengthening means is composed of a single material, in particular a partially bioabsorbable material.

Alternatively, the mesh is composed of a single material, in particular a bioabsorbable material.

Advantageously, the configuration in which the strengthening means is composed of a single partially bioabsorbable material, and in which the mesh is composed of a single bioabsorbable material, is intended for a case where it is chiefly necessary to maintain local reinforcement of the biological tissue and not reinforcement over the entirety of the surface of the prosthesis.

If necessary, the strengthening means may also be used to reinforce a central part fo the mesh. According to one embodiment, in a position fastened to the mesh, the strengthening means further covers a central part of one of said first and second faces of the mesh. With this configuration, it is possible to use a mesh of which the pores are of a considerable size. Indeed, the mechanical performance of the mesh, potentially reduced on account of the large size of the pores, is specifically compensated at the centre of the prosthesis by the strengthening means. Thus, the tissue integration of the prosthesis is improved without thereby compromising the reinforcement function needed at its centre to avoid a recurrence.

According to a embodiment, the strengthening means is made of partially bioabsorbable material and covers the central part of the mesh made of bioabsorbable material of which the size of the pores is greater than that of the pores of the strengthening means. This configuration is advantageous in that the mesh is reinforced at its centre and may thus have pores of greater dimensions. Moreover, the material of the mesh disappears over the course of time, whereas that of the strengthening means disappears partially in order to retain a sufficient mechanical stability in the area of the tissue defect, while limiting the quantity of foreign material present in the long term in the human body.

According to another configuration, it is advantageous to make available a prosthesis comprising a strengthening means made of bioabsorbable material covering the central part of the mesh made of partially absorbable material of which the size of the pores is larger than that of the pores of the strengthening means. The central reinforcement of the prosthesis is thus provided during the period of tissue rehabilitation, and the mesh with large pores remains partially on the entirety of the surface of the initial prosthesis while reducing the quantity of residual foreign material in the body.

In a position fastened to the mesh, the strengthening means covers a peripheral part of one of said first and second faces of the mesh. This configuration is particularly advantageous when the peripheral part of the prosthesis is intended to be fixed by staples or sutures to the biological wall. Indeed, the operation of stapling or suturing the mesh is susceptible to damaging the latter and even causing a local tear. Even though the mesh is designed so as not to propagate this tear, the presence of the strengthening means on the peripheral part of the mesh permits its mechanical reinforcement and affords added safety. This configuration makes it possible in fact to distribute, between the mesh and the strengthening means, the very local forces applied by the suturing or stapling of the prosthesis to the wall. Moreover, this peripheral reinforcement facilitates the deployment and positioning of the prosthesis by local stiffening of the mesh.

When covering a peripheral part of the mesh, it is possible to use a mesh with large pores and made of a partially absorbable material combined with a strengthening means made of bioabsorbable material, such that the strengthening means disappears once the prosthesis has been fixed to the biological wall.

In a configuration in which the size of the pores of the strengthening means is smaller than the size of the pores of the mesh, and the size of the pores of the mesh is too large to permit stapling, it is also very advantageous to use a strengthening means covering a peripheral part of the mesh.

According to one embodiment, at least a part of the strengthening means comprises a colour distinct from that of the mesh. This makes it easier for the surgeon to position and fix the prosthesis despite the lack of space and lack of visibility of the operating site. For example, when the strengthening means covers the peripheral part of the mesh, it is easy to identify the peripheral edges of the prosthesis according to the invention in order to fix it to the biological wall.

In one embodiment, the colour of the textile of the strengthening means and the colour of the mesh generate a contrast of 50% to 100%, preferably of 70% to 100%, according to the scale of contrast sensitivity defined for public buildings. In the present application, the contrast is determined according to the scale of contrast sensitivity (Functional Acuity Contrast Test) defined for public buildings by Dr Arthur Ginsburg, illustrated by Table I below:

TABLE I

| contrast in %, according to the scale of contrast sensitivity defined for public buildings | | | | | | | | | | | | |
|---|---|---|---|---|---|---|---|---|---|---|---|---|
| | Beige | White | Grey | Black | Brown | Pink | Purple | Green | Orange | Blue | Yellow | Red |
| Red | 78 | 84 | 32 | 38 | 7 | 57 | 28 | 24 | 62 | 13 | 82 | 0 |
| Yellow | 14 | 16 | 73 | 89 | 80 | 58 | 75 | 76 | 52 | 79 | 0 | |
| Blue | 75 | 82 | 21 | 47 | 7 | 50 | 17 | 12 | 56 | 0 | | |
| Orange | 44 | 60 | 44 | 76 | 59 | 12 | 47 | 50 | 0 | | | |
| Green | 72 | 80 | 11 | 53 | 18 | 43 | 6 | 0 | | | | |
| Purple | 70 | 79 | 5 | 56 | 22 | 40 | 0 | | | | | |
| Pink | 51 | 65 | 37 | 73 | 53 | 0 | | | | | | |
| Brown | 77 | 84 | 26 | 43 | 0 | | | | | | | |
| Black | 87 | 91 | 58 | 0 | | | | | | | | |
| Grey | 69 | 78 | 0 | | | | | | | | | |
| White | 28 | 0 | | | | | | | | | | |
| Beige | 0 | | | | | | | | | | | |

As will be seen from Table I above, the textile colour/mesh colour combinations suitable for the prosthesis of the invention can be chosen from among the following combinations: beige/red, beige/blue, beige/green, beige/purple, beige/pink, beige/brown, beige/black, beige/grey, white/red, white/blue, white/orange, white/green, white/purple, white/pink, white/brown, white/black, white/grey, grey/yellow, grey/black, black/yellow, black/orange, black/green, black/purple, black/pink, brown/yellow, brown/orange, brown/pink, pink/red, pink/yellow, pink/blue, purple/yellow, green/yellow, green/orange, orange/red, orange/yellow, orange/blue, blue/yellow, yellow/red.

Advantageously, the prosthesis comprises fixing means intended to fix the prosthesis to biological tissues. It is thus easy to fix the prosthesis according to the invention without having to use external elements such as staples, and without the need for suture points.

According to one embodiment, the fixing means are situated on the strengthening means and/or on one or both of said first and second faces of the mesh. This permits reinforced fixing of the prosthesis to biological tissue. For example, when the strengthening means is positioned between the biological wall and the mesh, the surface of the strengthening means and the surface of the mesh in contact with the wall to be strengthened can both have fixing means, so as to reinforce the fixing of the prosthesis to the wall.

The fixing means preferably comprise barbs. They are easily produced from the mesh and from the strengthening means by techniques well known to a person skilled in the art. Thus, when the fastening means are also barbs, the fastening means can have the function of the fixing means, and vice versa. The use of the prosthesis is thereby simplified.

Other aspects, aims and advantages of the present invention will become clearer from reading the following description of three embodiments thereof, which description is given as a non-limiting example and with reference to the attached drawings. In order to improve their legibility, the figures do not necessarily reflect the scale of all the elements shown. To make matters simpler in the remainder of the description, identical, similar or equivalent elements in the different embodiments bear the same reference numbers.

Figure 1:
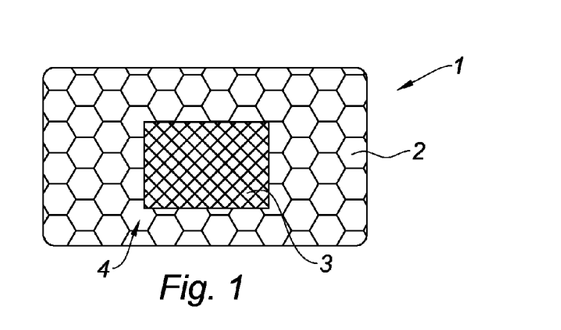
FIG. 1 shows a plan view of a prosthesis according to one embodiment of the invention.

FIG. 1 shows a plan view of a prosthesis 1 according to the invention suitable for medical or surgical use. The prosthesis 1 comprises a porous mesh 2 made of biocompatible material, and a strengthening means in the form of a piece of textile 3 made of porous biocompatible material. This piece of textile 3 covers a central part 4 of the mesh 2 so as to strengthen said part. The pores of the piece of textile 3 have a smaller size than that of the pores of the mesh 2, so as to give the mesh 2 mechanical strength and resistance to elongation at the location of the covering. The large size of the pores of the mesh 2, for example 1.5 mm×1.5 mm, or preferably 3 mm×3 mm, makes it possible to reduce the amount of residual foreign material in the body of the patient and to promote cell colonization.

Figures 2, 3, 4, 5, 6:
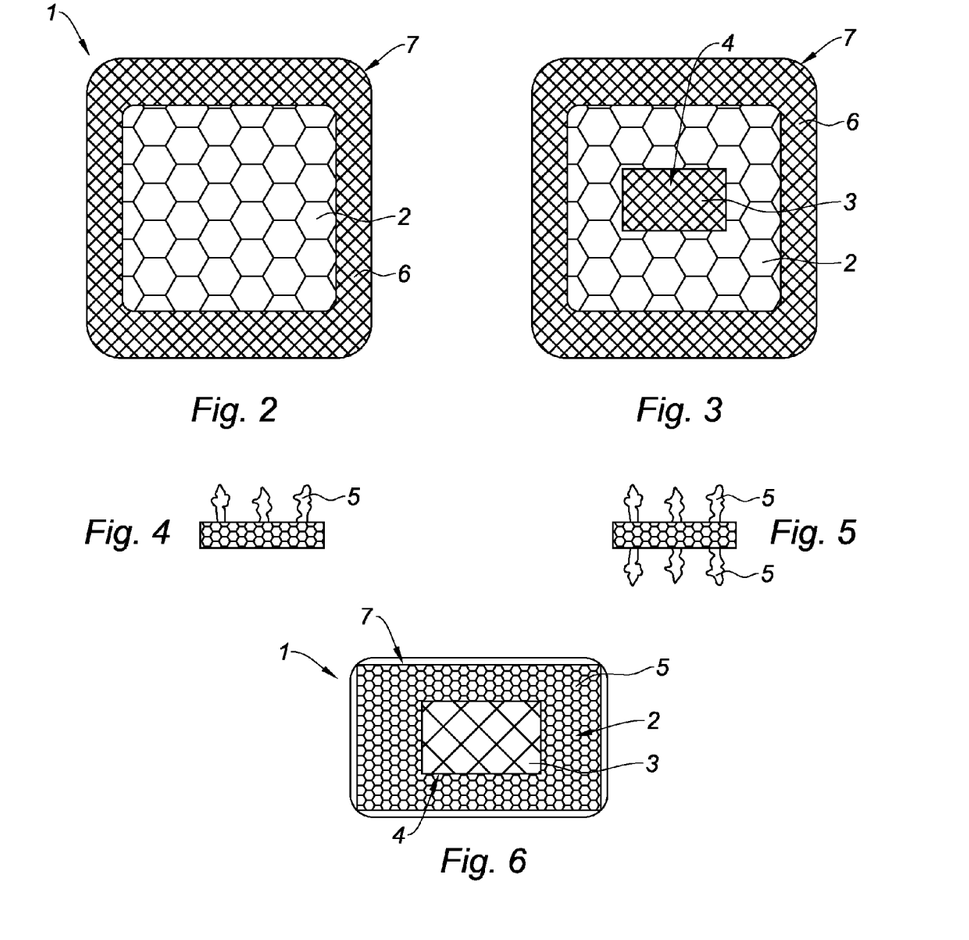
FIG. 2 shows a plan view of a prosthesis according to another embodiment of the invention.
FIG. 3 shows a plan view of a prosthesis according to yet another embodiment of the invention.
FIG. 4 shows a sectional view of a fastening means of a prosthesis according to one embodiment of the invention.
FIG. 5 shows a sectional view of a fastening means of a prosthesis according to another embodiment of the invention.
FIG. 6 shows a plan view of a prosthesis according to a third embodiment of the invention.

The piece of textile 3 is fastened to the central part 4 of the mesh 2 by fastening means such as barbs 5, which are shown in FIG. 4. Although not visible in FIG. 1, the barbs 5 are present on the face of the piece of textile 3 in contact with the mesh 2. A piece of textile 3 of this kind, for example in the form of a knit comprising barbs 5 on one face, is described in WO01/81667. According to a variant shown in FIG. 5, the barbs 5 can also be present on both faces of the piece of textile 3, so as to form means for fixing to biological tissues.

According to another variant not shown, the barbs 5 are present on the first face of the mesh 2 for fastening to the strengthening means, for example the piece of textile 3. According to yet another possibility not shown, the barbs 5 are present on the first and second faces of the mesh 2. The barbs 5 of one of the faces of the mesh 2 can also serve there as means for fixing to biological tissues.

According to another combination not shown, the barbs 5 are present on the first and second faces of the mesh 2 and on the strengthening means, for example the piece of textile 3.

According to one possibility not visible in the figures, the material of the mesh 2 is composed of a bioabsorbable material, and the material of the strengthening means, for example the piece of textile 3, is composed of a partially bioabsorbable material. Over the course of time, the mesh 2 disappears and the residual non-bioabsorbable part of the strengthening means (for example the piece of textile 3) continues to strengthen the region of the tissue defect.

FIG. 2 shows a prosthesis 1 according to the invention comprising a mesh 2 and a strengthening means in the form of a porous nonwoven textile 6 covering a peripheral part 7 of the mesh 2 by being fastened thereto. This embodiment is particularly advantageous when the object is to strengthen the peripheral part 7 of the mesh 2 susceptible to fraying during the stapling to the biological tissues. The mesh 2 is then composed of a partially biodegradable material, so as to ensure a permanent reinforcement over the whole of the initial surface of the prosthesis 1. Advantageously, the porous nonwoven textile 6 is made of bioabsorbable material in order to ensure its strengthening function at the time of stapling and then to disappear and leave behind a minimal quantity of foreign material.

As is shown in FIG. 2, the mesh 2 has pores of a size larger than that of the pores of the porous nonwoven textile 6. Thus, after a period of time, and once the porous nonwoven textile 6 has disappeared, only the non-biodegradable portion of mesh 2 with large pores remains. Therefore, this prosthesis 1 leaves little residual foreign material in the body of the patient.

FIG. 3 shows the prosthesis 1 according to the invention comprising a first strengthening means, for example a piece of textile 3, on a central part 4 of a mesh 2, and a second strengthening means, for example a porous nonwoven textile 6, on a peripheral part 7 of the mesh 2.

FIG. 4 shows barbs 5 present on one face of the mesh 2 and/or of a strengthening means, for example a piece of textile 3, according to the invention. FIG. 5 shows barbs 5 present on both faces of the mesh 2 and/or of a strengthening means, for example a piece of textile 3, according to the invention.

FIG. 6 shows a prosthesis 1 according to the invention in which a mesh 2 has a first face covered by barbs 5 for fastening a strengthening means, for example the piece of textile 3. With the strengthening means 3 being positioned in the central part 4 of the mesh 2, the barbs 5 of the peripheral part 7 of the mesh 2 are not used and can serve as means for fixing to biological tissue.

It is also conceivable that the face of the strengthening means, for example the piece of textile 3, in contact with the biological tissue is covered by barbs 5 for additional fixation (not shown).

In one variant, barbs 5 can be provided on the first and second faces of the mesh 2, as is shown in FIG. 5, such that the prosthesis 1 can be fixed to the biological tissue from the first or the second face of the mesh 2.

Thus, the prosthesis 1 of the invention can have any type of shape and can be manufactured very easily. The prosthesis 1 is simple to use and advantageously leaves little residual foreign material in the body of the patient.

It goes without saying that the invention is not limited to the embodiments described above by way of example and instead comprises all the technical equivalents and the variants of the means described and their combinations.

The invention claimed is:
1. A prosthesis for medical or surgical use comprising:
at least one porous mesh made of biocompatible material, the mesh comprising a first face, a second face opposite the first face, and a first set of barbs integral to and extending from the mesh and configured to attach the prosthesis to biological tissue, at least one strengthening means which strengthens the mesh and is intended to cover at least part of one of the first and second faces of the mesh, a second set of barbs integral to and extending from the strengthening means and configured to permit reversible fixation and renewed fixation of the strengthening means to the mesh, wherein the strengthening means is porous, pores of the mesh having dimensions larger than pores of the strengthening means, and, in a position fastened to the mesh, the strengthening means covers a peripheral part of one of the first and second faces of the mesh.

2. The prosthesis according to claim 1, wherein the strengthening means comprises a bioabsorbable material and the mesh comprises a partially bioabsorbable material.

3. The prosthesis according to claim 1, wherein the strengthening means comprises a partially bioabsorbable material and the mesh comprises a bioabsorbable material.

4. The prosthesis according to claim 1, wherein the strengthening means further covers a central part of one of the first and second faces of the mesh.

5. The prosthesis according to claim 1, wherein the first set of barbs are situated on one or both of the first and second faces of the mesh.

6. The prosthesis according to claim 1, wherein the strengthening means comprises at least one piece of a textile made of biocompatible material.

7. The prosthesis according to claim 6, wherein the textile comprises a color distinct from a color of the mesh.

8. The prosthesis according to claim 7, wherein the color of the textile and the color of the mesh generate a contrast of 50% to 100% according to the scale of contrast sensitivity defined for public buildings.

9. The prosthesis according to claim 7, wherein the color of the textile and the color of the mesh generate a contrast of 70% to 100% according to the scale of contrast sensitivity defined for public buildings.

10. The prosthesis according to claim 7, wherein combinations of the color of the textile and the color of the mesh are selected from the group consisting of beige/red, beige/blue, beige/green, beige/purple, beige/pink, beige/brown, beige/black, beige/grey, white/red, white/orange, white/pink, white/brown, white/black, white/grey, grey/yellow, grey/black, black/yellow, black/orange, black/green, black/purple, black/pink, brown/yellow, brown/orange, brown/pink, pink/red, pink/yellow, pink/blue, purple/yellow, green/yellow, green/orange, orange/red, orange/yellow, orange/blue, blue/yellow, and yellow/red.

11. A prosthesis for medical or surgical use comprising at least one porous mesh made of biocompatible material, the mesh comprising a first face, a second face opposite the first face, and a first set of barbs for attaching the mesh to biological tissue, a first nonwoven textile made of a porous biocompatible material which strengthens the mesh and covers a peripheral part of at least one of the first and second faces of the mesh, the first nonwoven textile including a second set of barbs for fastening the first nonwoven textile to the peripheral part of the mesh, wherein pores of the mesh have dimensions larger than pores of the first nonwoven textile.

* * * * *